United States Patent
Asada et al.

(10) Patent No.: US 8,314,836 B2
(45) Date of Patent: Nov. 20, 2012

(54) MEDICAL CAPSULE INCLUDING SHAKE ABSORPTION SECTION AND INDWELLED AND FIXED IN VIVO

(75) Inventors: Daisuke Asada, Hachioji (JP); Sho Nakajima, Hachioji (JP); Nobuyoshi Yazawa, Hachioji (JP)

(73) Assignee: Olympus Medical Systems Corp., Tokyo (JP)

(*) Notice: Subject to any disclaimer, the term of this patent is extended or adjusted under 35 U.S.C. 154(b) by 0 days.

(21) Appl. No.: 13/012,073

(22) Filed: Jun. 14, 2011

(65) Prior Publication Data

US 2011/0254938 A1    Oct. 20, 2011

Related U.S. Application Data

(63) Continuation of application No. PCT/JP2010/066377, filed on Sep. 22, 2010.

(30) Foreign Application Priority Data

Feb. 8, 2010    (JP) .................................. 2010-025775

(51) Int. Cl.
*A61B 1/04* (2006.01)
(52) U.S. Cl. .......................................... 348/76; 348/75
(58) Field of Classification Search .................... 348/75, 348/76
See application file for complete search history.

(56) References Cited

U.S. PATENT DOCUMENTS

| | | | |
|---|---|---|---|
| 5,984,860 | A | 11/1999 | Shan |
| 6,290,656 | B1* | 9/2001 | Boyle et al. .................... 600/585 |
| 2008/0208003 | A1* | 8/2008 | Miyagi et al. ................. 600/146 |

FOREIGN PATENT DOCUMENTS

| | | |
|---|---|---|
| JP | 2002-204773 | 7/2002 |
| JP | 2009-517123 | 4/2009 |
| WO | WO 2007/061386 A1 | 5/2007 |

* cited by examiner

*Primary Examiner* — Jay Patel
*Assistant Examiner* — Richard Torrente
(74) *Attorney, Agent, or Firm* — Scully, Scott, Murphy & Presser, PC

(57) ABSTRACT

A medical apparatus of the present invention includes an image pickup apparatus provided for a medical instrument to pick up an image of a region to be examined in a body, a fixing section that keeps the image pickup apparatus indwelling in and fixed to a body wall in the body, a transmission section that extends from the image pickup apparatus and transmits a power or an electric signal to/from a device outside the body, and a shake absorption section that absorbs and suppresses shaking of the transmission section by means of a movable member connected to the transmission section and freely movable with respect to the image pickup apparatus and a holding member connected to the transmission section for holding the movable member in a freely movable manner, wherein when a treatment is applied to a subject in the body while observing the subject, the apparatus can suppress shaking of the image pickup apparatus left indwelling in the body, acquire an excellent observed image and prevent damage to a cable extending from the image pickup apparatus.

7 Claims, 11 Drawing Sheets

MEDICAL CAPSULE INCLUDING SHAKE ABSORPTION SECTION AND INDWELLED AND FIXED IN VIVO

CROSS REFERENCE TO RELATED APPLICATION

This application is a continuation application of PCT/JP2010/066377 filed on Sep. 22, 2010 and claims benefit of Japanese Application No. 2010-025775 filed in Japan on Feb. 8, 2010, the entire contents of which are incorporated herein by this reference.

BACKGROUND OF THE INVENTION

1. Field of the Invention

The present invention relates to a medical instrument provided with an image pickup apparatus which is left indwelling in and fixed to a body to pick up an image of a subject.

2. Description of the Related Art

As is generally known, endoscope apparatuses, which are medical instruments, are provided with an image pickup apparatus which is image pickup means, designed to be introduced into a body cavity of a patient and perform various kinds of inspections and treatment or the like of a diseased part in the body based on observed images taken by the image pickup apparatus. Examples of such endoscope apparatuses include those introduced into digestive organs such as esophagus, stomach, large intestine, duodenum, which are tube cavities and tubes in the body from the oral cavity or anus and those introduced into the abdominal cavity from the vicinity of the umbilical region by puncturing through the body wall. Various proposals are presented for such medical instruments like endoscope apparatuses as follows.

For example, Japanese Patent Application Laid-Open Publication No. 2009-517123 discloses an apparatus for operation under laparoscopy or operation under thoracoscopy provided with a first member which moves along a patient's body and a second member which is arranged in the body and is provided with an image acquiring apparatus to acquire an image from the interior of the body and send the acquired image to be displayed, wherein the second member is magnetically linked with the first member so that the movement of the second member in the body corresponds to the movement of the first member along the body. The conventional apparatus for operation under laparoscopy or operation under thoracoscopy has a configuration in which a flexible cable extends from the image acquiring apparatus, the cable is pulled out of the body and connected to a display apparatus and a power supply.

SUMMARY OF THE INVENTION

A first medical apparatus according to one aspect of the present invention is provided with an image pickup apparatus provided for a medical instrument to pick up an image of a region to be examined in a body, a fixing section that keeps the image pickup apparatus indwelling in and fixed to a body wall in the body, a transmission section that extends from the image pickup apparatus and transmits a power or an electric signal to/from a device outside the body, and a shake absorption section that absorbs and suppresses shaking of the transmission section by means of a movable member connected to the transmission section and freely movable with respect to the image pickup apparatus and a holding member connected to the transmission section for holding the movable member in a freely movable manner.

DETAILED DESCRIPTION OF THE PREFERRED EMBODIMENT(S)

Hereinafter, a medical instrument provided with image pickup means used for laparoscopic surgical operation or the like will be described below as an example of the present invention. In the following descriptions, it should be noted that drawings based on each embodiment are schematic ones and a relationship between thickness and width of each portion, and a ratio of thickness between the respective portions are different from real ones, and the drawings may also include portions whose dimensional relationship and ratio differ between the drawings.

First Embodiment

Figure 1:
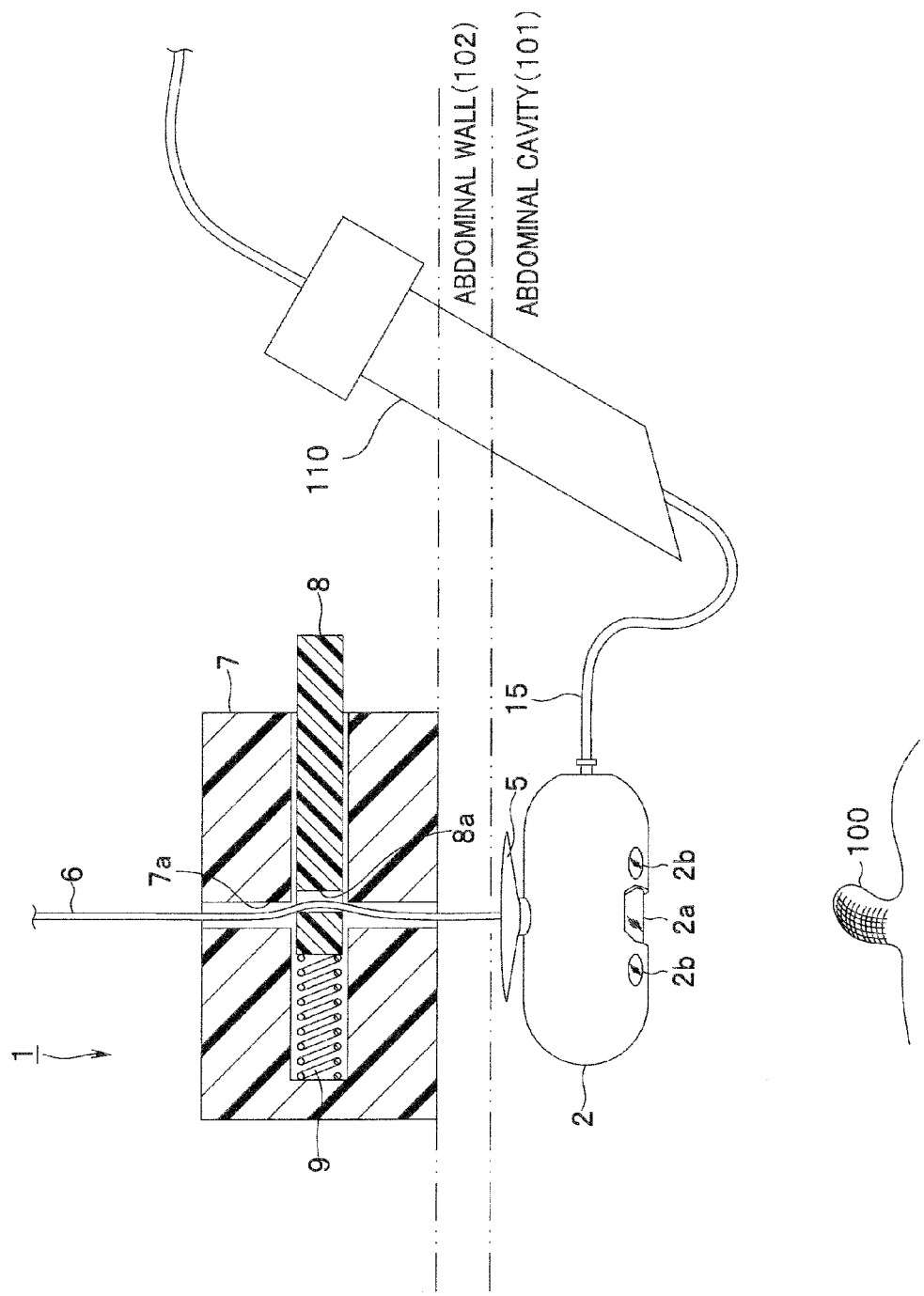
FIG. 1 is related to a first embodiment of the present invention, schematically illustrating a configuration of a camera set up in the abdominal cavity when set up in the abdominal cavity.
Figure 2:
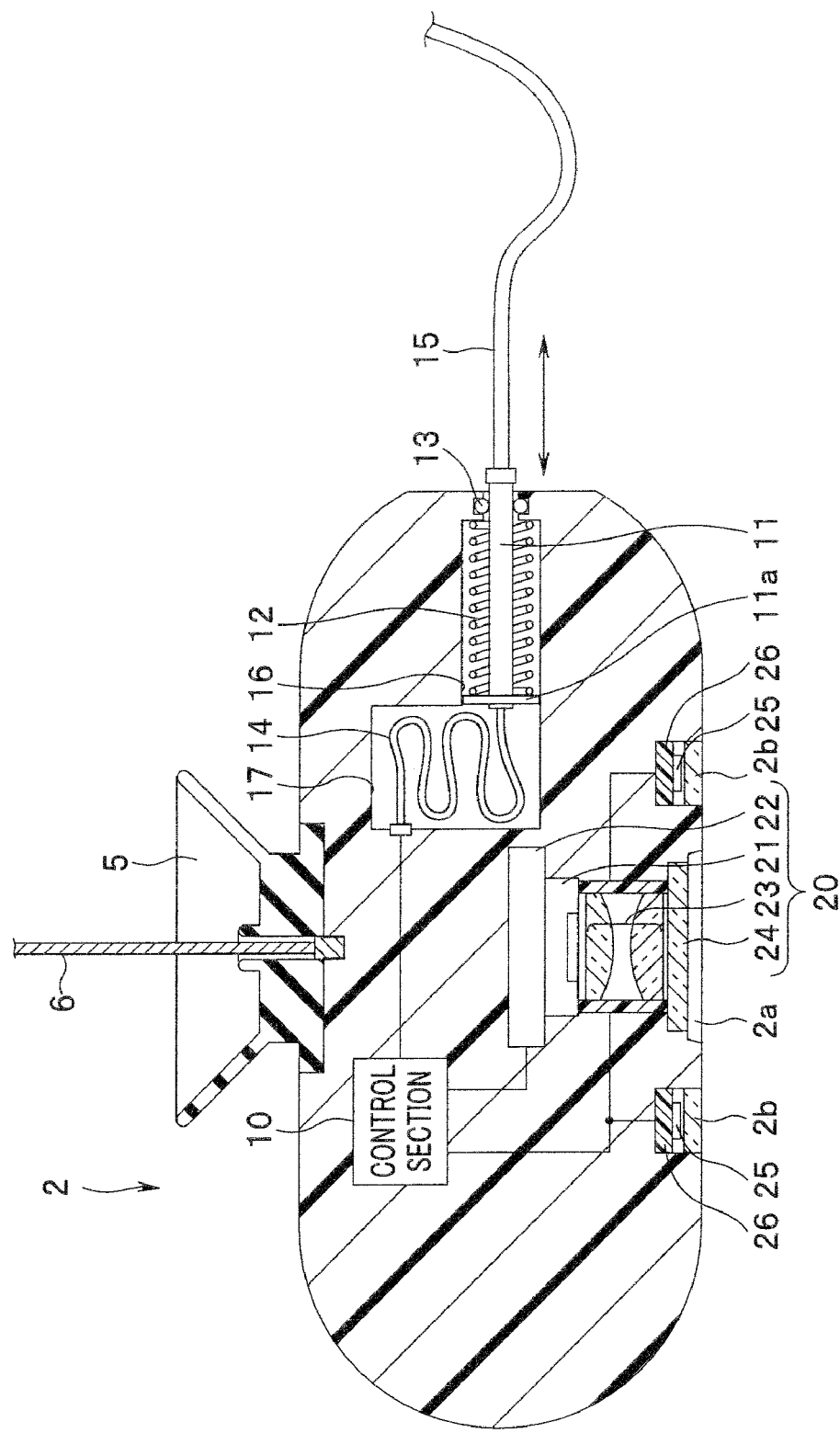
FIG. 2 is a cross-sectional view illustrating an internal configuration of the camera set up in the abdominal cavity according to the first embodiment of the present invention.
Figure 3:
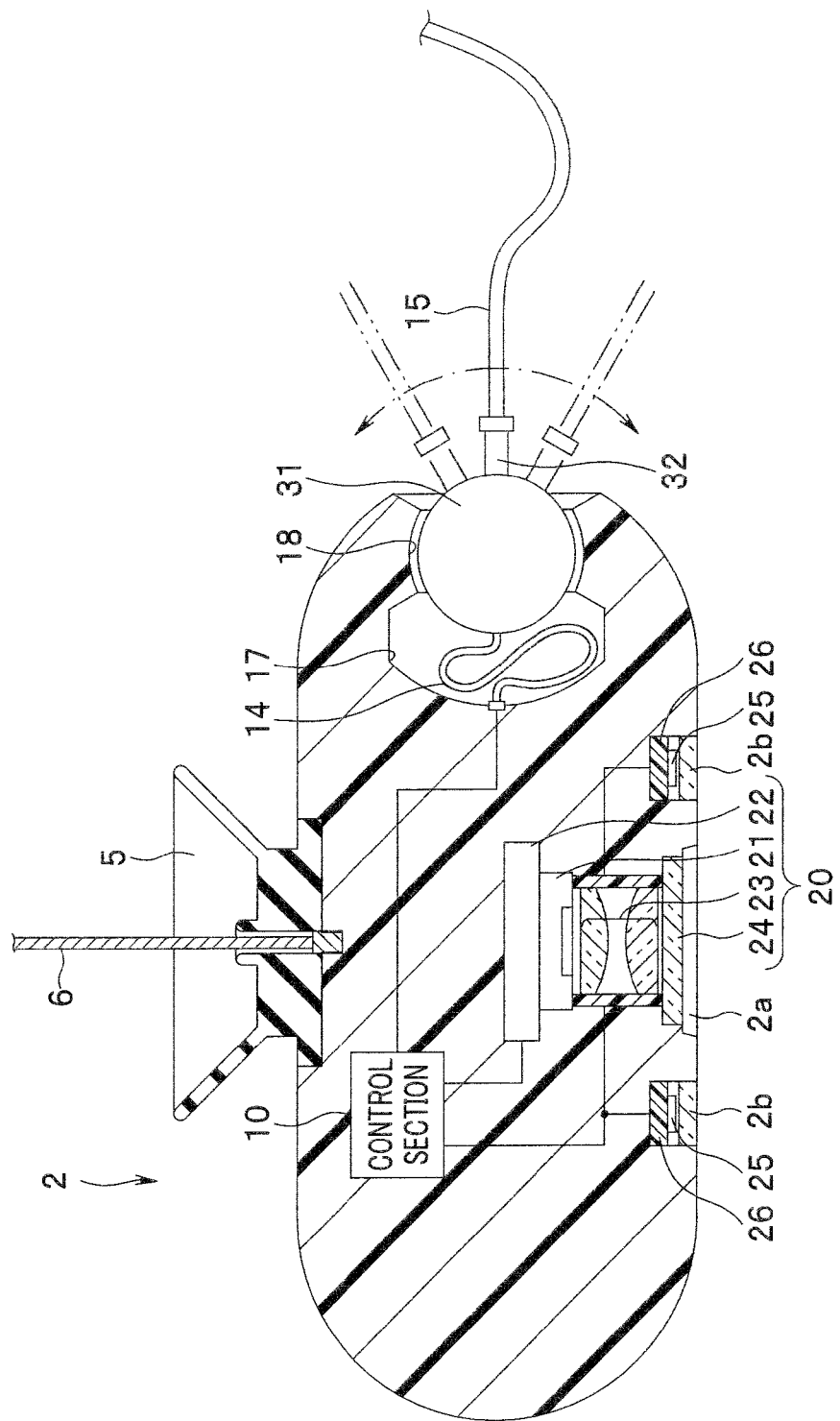
FIG. 3 is a cross-sectional view illustrating an internal configuration of the camera set up in the abdominal cavity according to a modification example of the first embodiment of the present invention.

First, a medical apparatus of the present invention used for laparoscopic surgical operation will be described based on FIG. 1 to FIG. 3 below. FIG. 1 to FIG. 3 are related to a first embodiment of the present invention; FIG. 1 is a diagram schematically illustrating a configuration of a camera set up in the abdominal cavity when set up in the abdominal cavity, FIG. 2 is a cross-sectional view illustrating an internal configuration of the camera set up in the abdominal cavity and FIG. 3 is a cross-sectional view illustrating an internal configuration of a modification example of the camera set up in the abdominal cavity.

An abdominal cavity camera system (hereinafter simply referred to as "camera system") 1 which is a medical apparatus of the present embodiment is mainly configured by including a camera 2 set up in the abdominal cavity (hereinafter simply referred to as "camera") which is a medical instrument including image pickup means and a fixing unit 7 which is camera fixing means outside the body.

The camera 2 is a capsule-shaped, treatment or downward view camera with built-in image pickup means and is provided with a suction cup 5 which is an abdominal wall fixing section of fixing means inside the body attached at the top of the camera and a camera fixing wire 6 which extends from the center of the suction cup 5 and is fixed. Furthermore, a cable 15 extends from one end of the camera 2, connected to a video processor (not shown) which is a device outside the body and is transmission means for sending/receiving image signals and power. The cable 15 is arranged so as to extend to the outside of the body through a trocar 110 that is punctured into the abdominal cavity 101 so as to penetrate the abdominal wall 102.

The camera 2 is set to a predetermined viewing angle and provided with an observation window 2a for observation at the bottom of the outer circumference opposite to the top of the outer circumference where the suction cup 5 is provided and two illuminating windows 2b on both sides of the observation window 2a.

The camera 2 of the present embodiment is used for laparoscopic surgical operation and used to photograph a treatment instrument for an organ or the like in the abdominal cavity 101 which is one of body cavities of the patient and a diseased part 100 which is a region to be treated (region to be examined).

First, the camera 2 is introduced into the abdominal cavity 101 of the patient through the trocar 110 which is punctured in the abdominal wall 102. The camera fixing wire 6 is hooked onto the camera 2 using a puncture needle (not shown) or the like which is punctured in the abdominal cavity 101 and the camera fixing wire 6 is pulled out of the body so as to penetrate the abdominal wall 102 which is the body wall.

Next, the camera fixing wire 6 of the camera 2 is passed through a hole 7a in the fixing unit 7 provided on the abdomen side of the patient and pulled toward the abdominal wall 102 side. The camera 2 is then lifted so as to move closer to the abdominal wall 102 and the camera fixing wire 6 is pulled toward the outside of the body until the suction cup 5 sticks fast to the inner surface of the abdominal wall 102. Thus, the camera 2 is left indwelling and fixed inside the abdominal cavity 101 with the suction cup 5 sticking fast to the abdominal wall 102.

The fixing unit 7 is provided with a fixing lever 8 that fixes the camera fixing wire 6 of the camera 1 outside the body. A hole 8a is formed at a halfway point of the fixing lever 8 through which the camera fixing wire 6 penetrates and the hole 8a is biased toward one direction of the fixing unit 7 by a spring 9 provided in the fixing unit 7 so as to produce a difference in position between the hole 8a and the hole 7a of the fixing unit 7.

That is, by pushing in the fixing lever 8 inside the fixing unit 7 against an urging force of the spring 9 up to a position where the hole 7a of the fixing unit 7 substantially coincides with the hole 8a of the fixing lever 8, the user can easily pull the camera fixing wire 6. When the user releases the pushing of the fixing lever 8 into the fixing unit 7, the fixing lever 8 slides due to the urging force of the spring 9.

This produces a difference between the position of the hole 7a of the fixing unit 7 and the position of the hole 8a of the fixing lever 8 and the camera fixing wire 6 of the camera 1 that passes through the holes 7a and 8a is caught and fixed in the fixing unit 7. Thus, the camera 1 is left indwelling and fixed in a stable condition with the suction cup 5 sticking fast to the wall surface of the abdominal wall 102 inside the body within the abdominal cavity 101.

Next, as described above, a more specific configuration of the camera 2 left indwelling and fixed in the abdominal cavity 101 will be described here in detail using FIG. 2.

As shown in FIG. 2, the camera 2 incorporates a control section 10 which is a control substrate serving as control means, an image pickup unit 20 which is image pickup means (image pickup apparatus) electrically connected to the control section 10 and illumination sections 26 arranged on both sides of the image pickup unit 20 and each having an LED light source 25 here electrically connected to the control section 10.

The image pickup unit 20 which is an image pickup apparatus is configured by including a solid image pickup device 21 which is a CCD or CMOS, a substrate section 22 mounted with the solid image pickup device 21, an objective lens group 23 disposed ahead of the solid image pickup device 21 and a cover glass 24 disposed in an observation window 2a.

Furthermore, a cylindrical cylinder 11, to which one end of the cable 15 is connected and fixed, is slidably (movably forward/backward) accommodated and arranged in the camera 2. The cylinder 11 is accommodated in a cylinder accommodating spatial section 16 formed in the camera 2 and a flange section 11a is provided at one end in the inside of the camera 2.

A spring 12 which is a biasing member for biasing the cylinder 11 toward the inside of the camera 2 is disposed extrapolating the cylinder 11 with one end thereof contacting the flange section 11a in the cylinder accommodating spatial section 16. The other end of the cylinder 11 extends from the side of the camera 2 and is connected to the cable 15.

Furthermore, a bearing member 13 (or O-ring member 13) that slidably holds the cylinder 11 and also serves as sealing means for ensuring watertightness is provided in a portion on one side of the camera 2 where the cylinder accommodating spatial section 16 has an opening.

Furthermore, an inner cable 14 electrically connected to the control section 10 is accommodated at one end of the cylinder 11 in the camera 2. The inner cable 14 is electrically connected to the cable 15 fixed to the cylinder 11. The inner cable 14 is accommodated in loose form in a cable accommodating spatial section 17 which communicates with the cylinder accommodating spatial section 16 formed in the camera 2.

Thus, the camera 2 of the present embodiment is provided with shake absorption means making up a buffering section provided between the camera 2 and the cable 15 by arranging the cylinder 11 so as to freely advance and retract and providing the spring 12 that biases the cylinder 11 toward an inward direction.

In the camera system 1 of the present embodiment configured as shown above, during a treatment of the diseased part 100 while observing the diseased part 100 with the camera 2 left indwelling and fixed in the abdominal cavity 101 as shown in FIG. 1, even when the trocar 110 through which the cable 15 extending from the camera 2 passes in contact moves or a treatment instrument used contacts the cable 15 causing interference (contact), the cylinder 11 connected to the cable 15 slides (moves forward/backward) with respect to the camera 2. Therefore, shaking of the cable 15 is absorbed by the slide operation of the cylinder 11 and is less likely to be transmitted to the camera 2.

Therefore, shaking of the camera 2 is suppressed and shaking of an observed image acquired is suppressed. As a result, during a treatment of the diseased part 100, even when the trocar 110 through which the cable 15 passes moves or the treatment instrument or the like interferes with (contacts) the cable 15 causing the cable 15 to shake, shaking is less likely to occur in an observed image, and the camera 2 can thereby acquire an excellent observed image.

Moreover, even when the treatment instrument or the like interferes with (contacts) the cable 15, the cylinder 11 moves forward/backward and reduces overload. This prevents damage to the cable 15 as well.

As the shake preventing means provided for the camera 2, a configuration of connecting the camera 2 and the cable 15 via a ball joint mechanism as shown in FIG. 3 may also be adopted.

To be more specific, the cable 15 is connected and fixed to a cable connection portion 32 extending from a sphere 31. In the sphere 31, the inner cable 14 electrically connected to the cable 15 extends from the opposite side of the cable connection portion 32.

A hole 18 is formed in the camera 2, which has a spherical inner surface so as to contact the outer surface of the sphere 31 and movably hold the sphere 31. The hole 18 communicates with the cable accommodating spatial section 17 and has an opening on one side of the camera 2. The sphere 31 is movably held in the hole 18 of the camera 2 in such a way that the cable connection portion 32 protrudes from the opening of the hole 18.

Connected to the camera 2 and the cable 15 through the ball joint mechanism in this way, the sphere 31 is configured to be freely movable around the center with respect to the camera 2. The cable 15 connected to the cable connection portion 32 can also freely move around the center of the sphere 31 with respect to the camera 2 making shaking of the cable 15 less likely to transmit to the camera 2.

By adopting the configuration of shake preventing means of the ball joint mechanism, shaking is less likely to occur in an observed image during a treatment of the diseased part 100 even when the trocar 110 through which the cable 15 passes moves or the treatment instrument or the like interferes with (contacts) the cable 15 as described above, causing the cable 15 to shake, and the camera 2 can thereby acquire an excellent observed image.

As the configuration of the shake preventing means, a configuration may also be adopted in which the camera 2 and the cable 15 are connected via a bellows tube so that shaking of the cable 15 is absorbed and suppressed.

Second Embodiment

Next, an image pickup unit according to a second embodiment will be described below based on FIG. 4 to FIG. 13.

Figure 4:
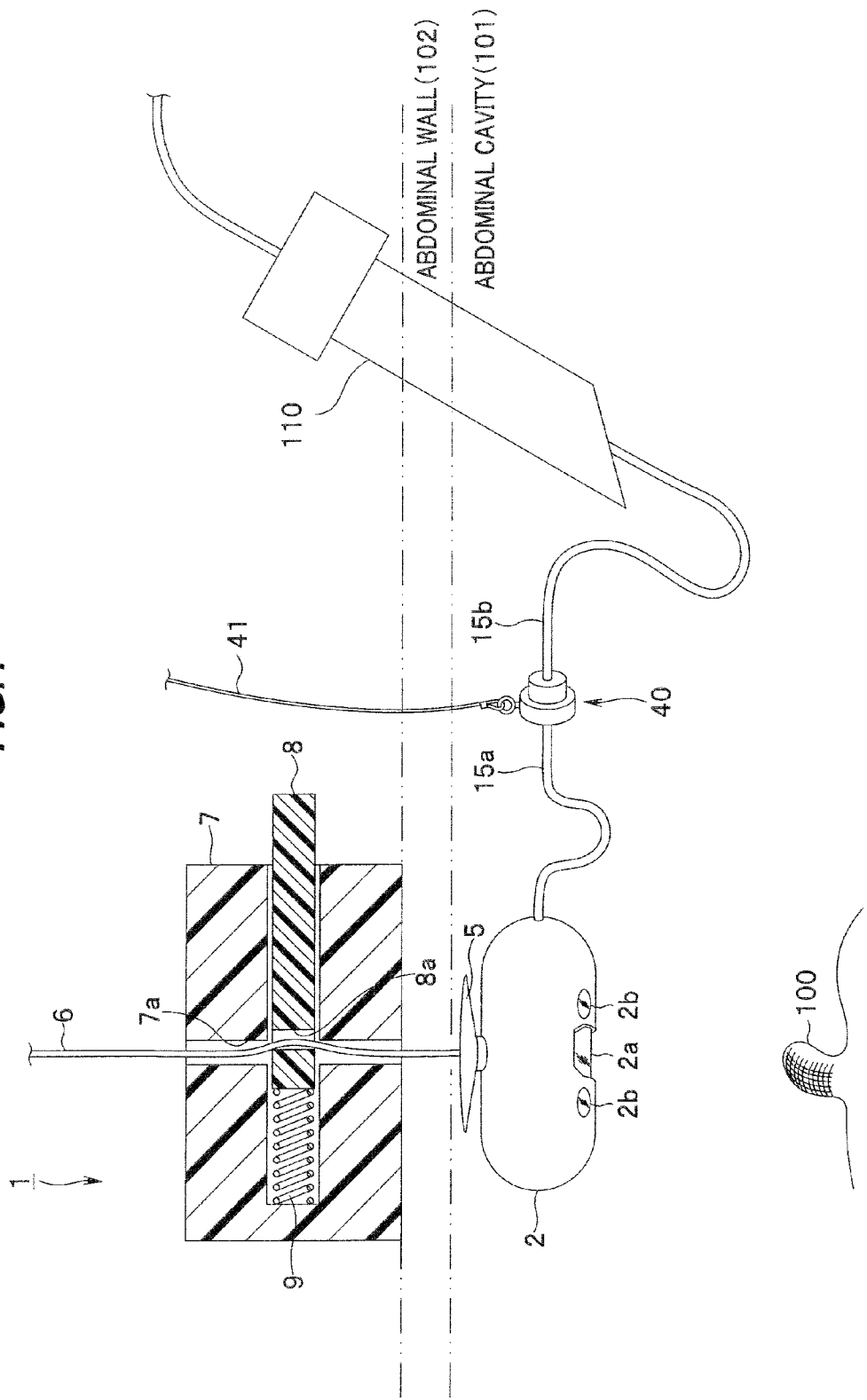
FIG. 4 is related to a second embodiment of the present invention, schematically illustrating a configuration of a camera set up in the abdominal cavity when set up in the abdominal cavity.
Figure 5:
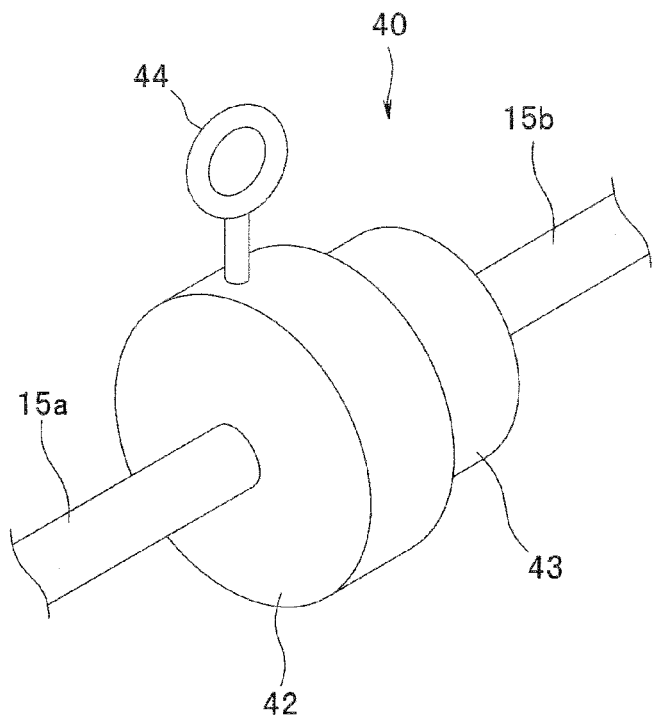
FIG. 5 is a perspective view illustrating a configuration of a cable shake absorption apparatus of the camera set up in the abdominal cavity according to the second embodiment of the present invention.
Figure 6:
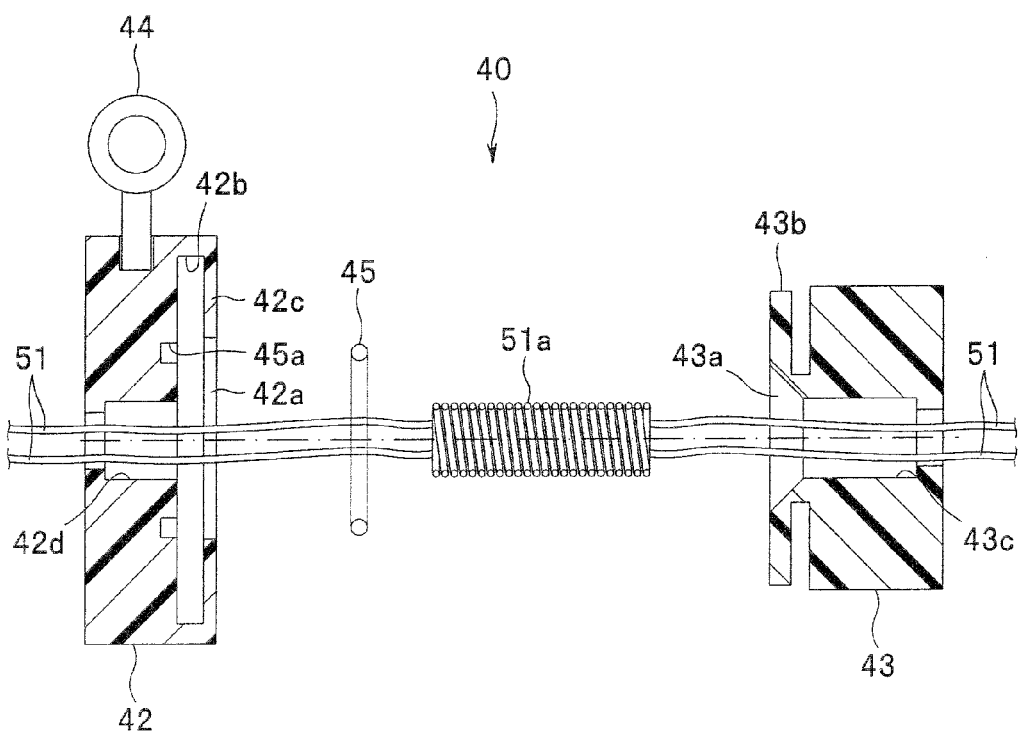
FIG. 6 is an exploded cross-sectional view illustrating a configuration of the cable shake absorption apparatus of the camera set up in the abdominal cavity according to the second embodiment of the present invention.
Figure 7:
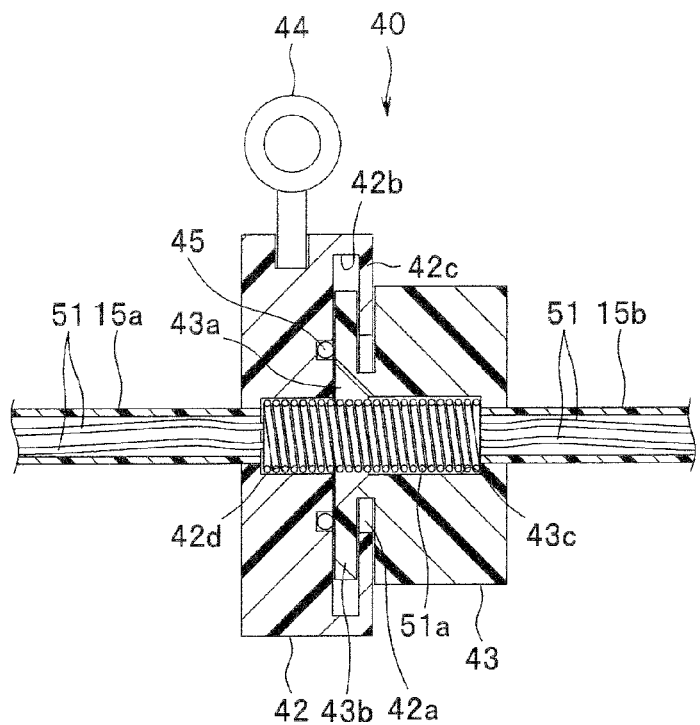
FIG. 7 is a cross-sectional view illustrating the configuration of the cable shake absorption apparatus of the camera set up in the abdominal cavity according to the second embodiment of the present invention.
Figure 8:
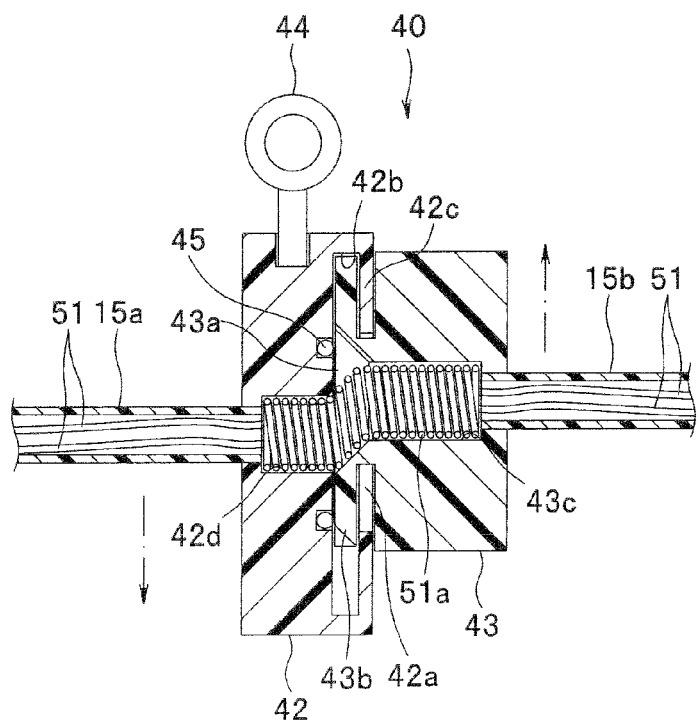
FIG. 8 is a cross-sectional view illustrating operation of the cable shake absorption apparatus of the camera set up in the abdominal cavity according to the second embodiment of the present invention.
Figure 9:
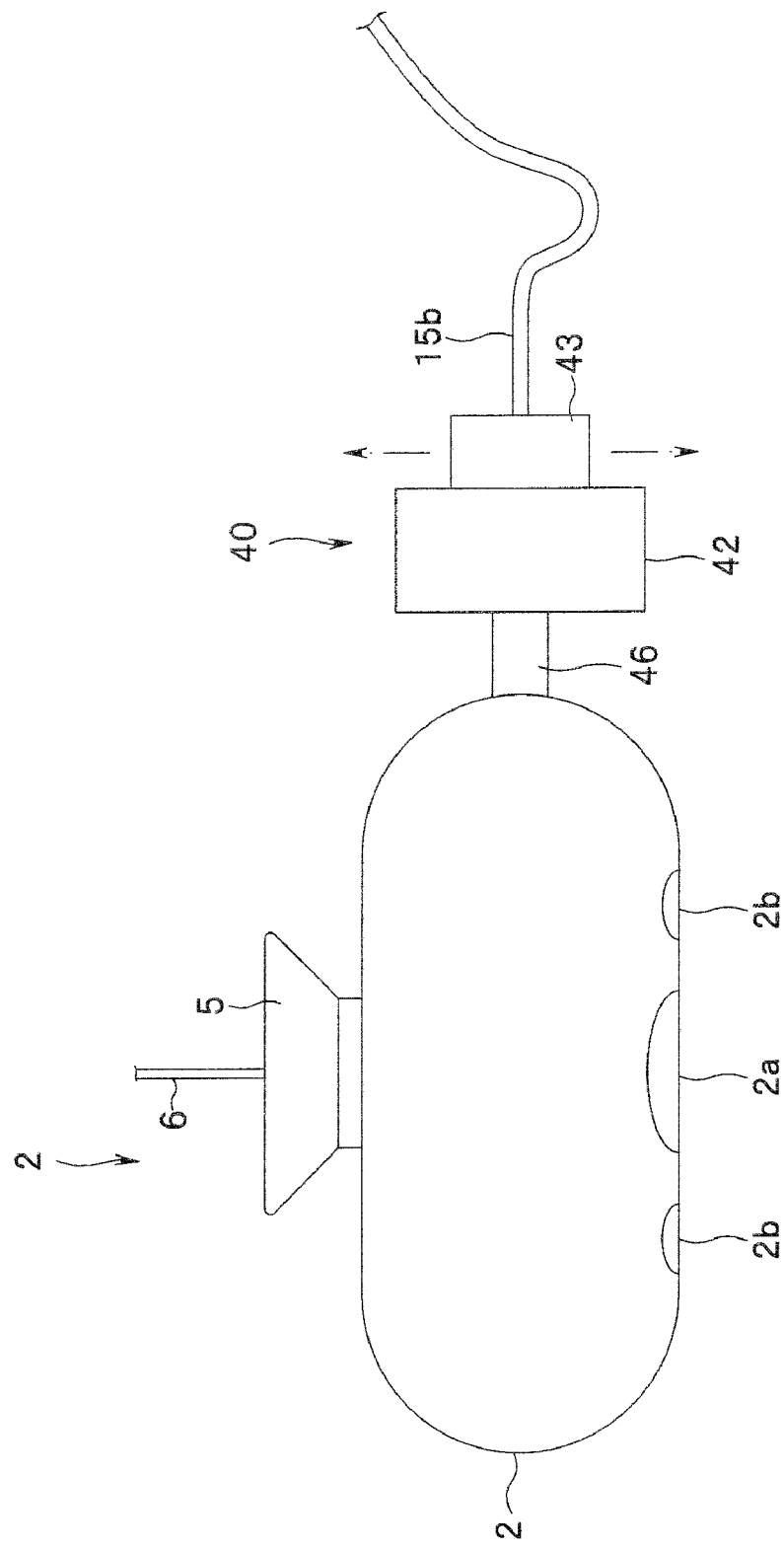
FIG. 9 shows a first modification example of the camera set up in the abdominal cavity according to the second embodiment of the present invention, illustrating a configuration of the camera set up in the abdominal cavity connected to the shake absorption apparatus using a rigid body cable.
Figure 10:
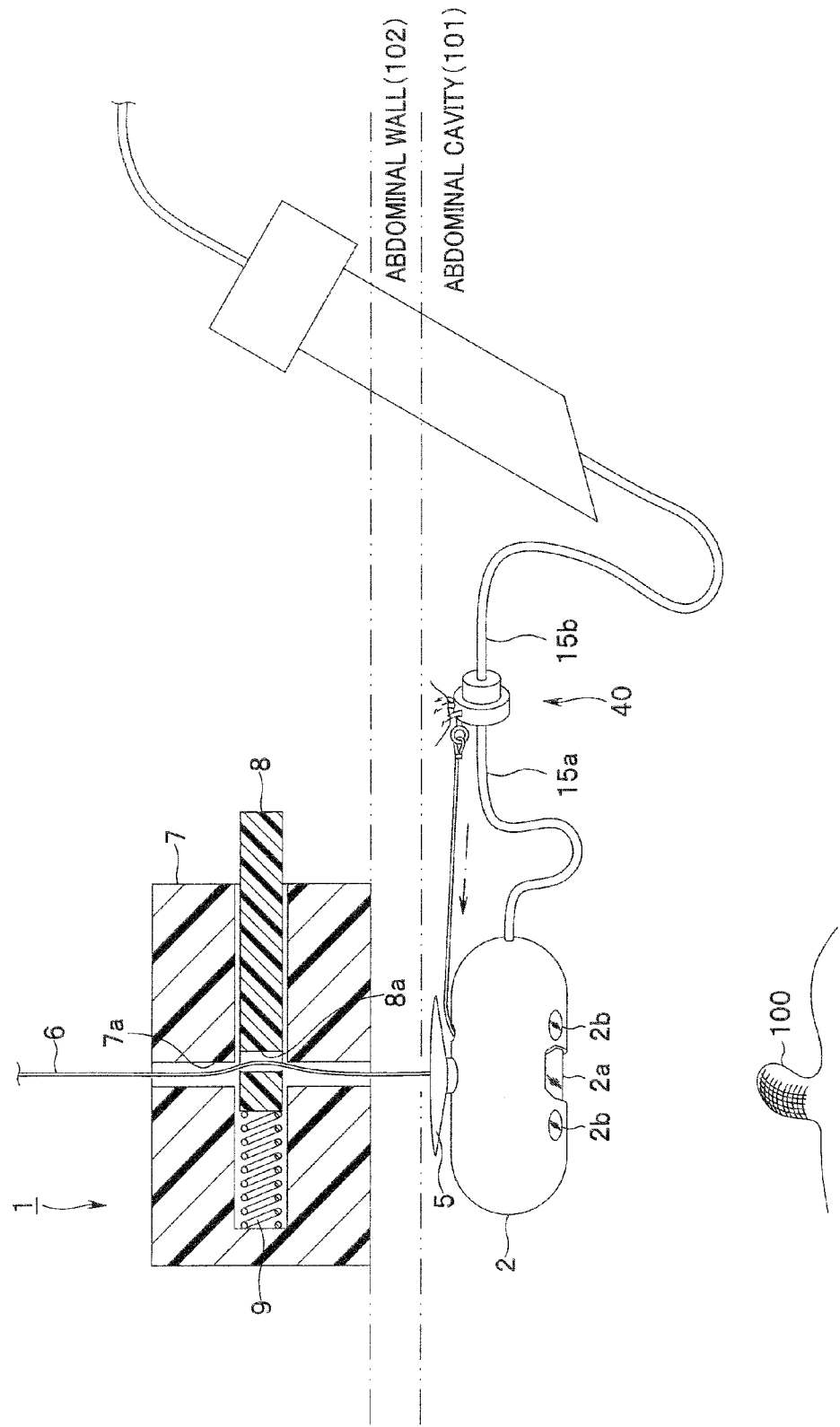
FIG. 10 shows a second modification example of the camera set up in the abdominal cavity according to the second embodiment of the present invention, schematically illustrating a configuration of the camera set up in the abdominal cavity when set up in the abdominal cavity.
Figure 11:
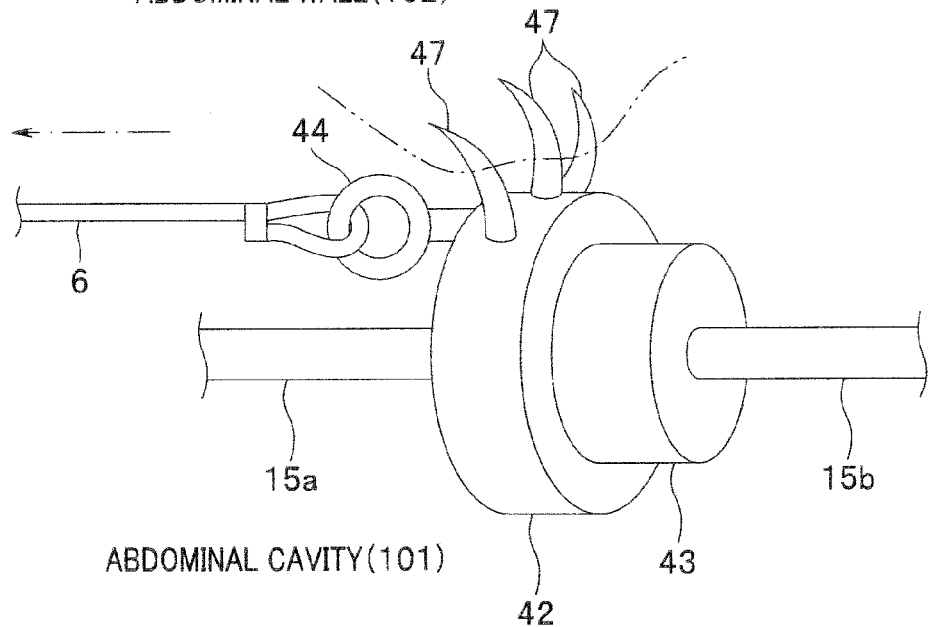
FIG. 11 is a perspective view illustrating a configuration of the cable shake absorption apparatus in FIG. 10 of the camera set up in the abdominal cavity according to the second modification example of the second embodiment of the present invention.
Figure 12:
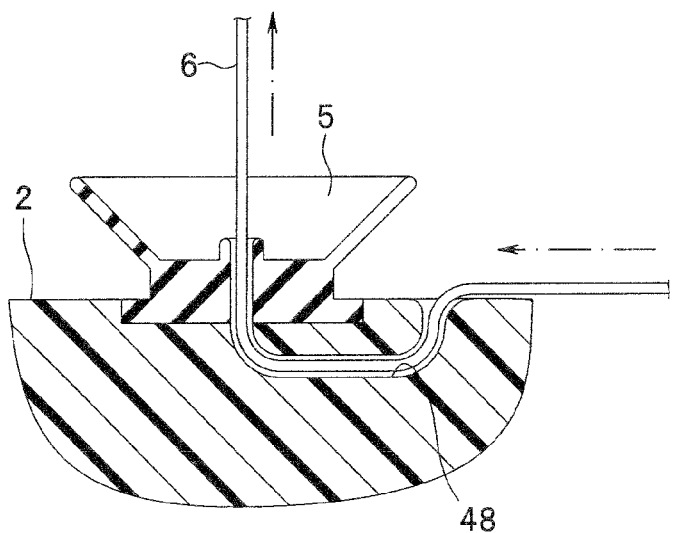
FIG. 12 is a partial cross-sectional view illustrating a wire to be inserted into the camera set up in the abdominal cavity in FIG. 10 according to the second modification example of the second embodiment of the present invention.
Figure 13:
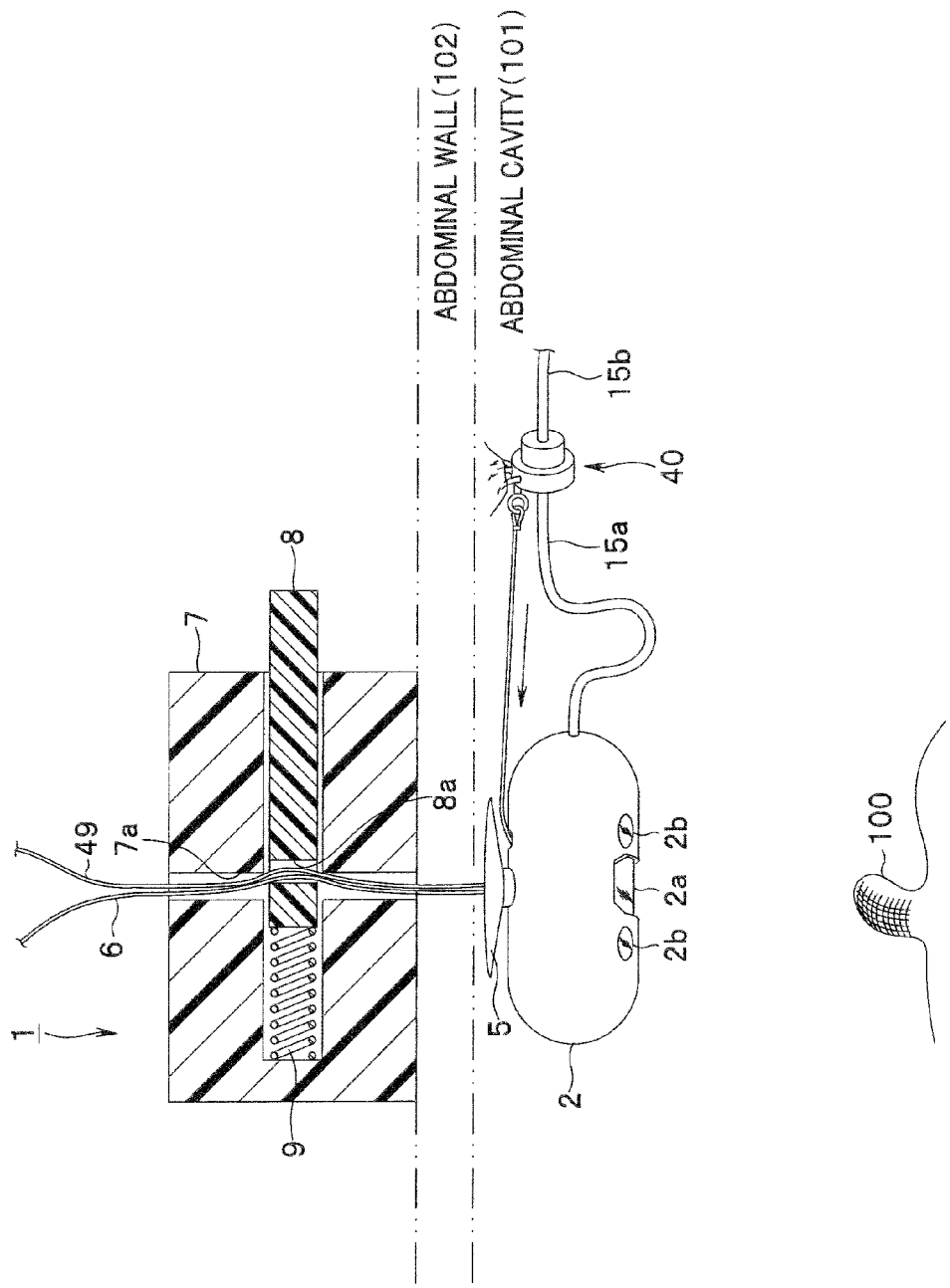
FIG. 13 shows a third modification example of the camera set up in the abdominal cavity according to the second embodiment of the present invention, schematically illustrating a configuration of the camera set up in the abdominal cavity when set up in the abdominal cavity.

FIG. 4 to FIG. 13 are related to the second embodiment of the present invention; FIG. 4 is a diagram schematically illustrating a configuration of a camera set up in the abdominal cavity when set up in the abdominal cavity, FIG. 5 is a perspective view illustrating a configuration of a cable shake absorption apparatus, FIG. 6 is an exploded cross-sectional view illustrating the configuration of the cable shake absorption apparatus, FIG. 7 is a cross-sectional view illustrating the configuration of the cable shake absorption apparatus, FIG. 8 is a cross-sectional view illustrating operation of the cable shake absorption apparatus, FIG. 9 shows a first modification example, illustrating a configuration of the camera set up in the abdominal cavity connected to the shake absorption apparatus using a rigid body cable, FIG. 10 shows a second modification example, schematically illustrating a configuration of the camera set up in the abdominal cavity when set up in the abdominal cavity, FIG. 11 is a perspective view illustrating a configuration of the cable shake absorption apparatus in FIG. 10, FIG. 12 is a partial cross-sectional view illustrating a wire to be inserted into the camera in FIG. 10 and FIG. 13 shows a third modification example, schematically illustrating a configuration of the camera set up in the abdominal cavity when set up in the abdominal cavity. Furthermore, in the following descriptions, the same components as those in the first embodiment will be assigned the same reference numerals and detailed descriptions, operations and effects thereof will be omitted for convenience of explanation.

As shown in FIG. 4, an abdominal cavity camera system (hereinafter simply referred to as "camera system") 1 of the present embodiment has a cable shake absorption apparatus 40 which is provided at a halfway point of a cable 15 (illustrated here as cables 15a and 15b) extending from a camera set up in the abdominal cavity (hereinafter simply referred to as "camera") 2 which is a medical instrument as a component independent of the camera 2 and is shake preventing means introduced into the abdominal cavity 101 and an apparatus lifting wire 41 which lifts the cable shake absorption apparatus 40 toward the abdominal wall 102 side. The cable 15a extending from the camera 2 is configured to be directly connected and fixed to one side of the camera 2. Furthermore, the apparatus lifting wire 41 is designed to be pulled out of the body from within the abdominal cavity 101 through a puncture needle (not shown) or the like so as to penetrate the abdominal wall 102.

As shown in FIG. 5 to FIG. 8, the cable shake absorption apparatus 40 of the present embodiment is configured by including a first block body 42 having a columnar outside shape, to the center of the front surface of which the cable 15a on the camera 2 side is connected and a second block body 43 having a columnar outside shape provided in a manner freely movable with respect to the first block body 42, the front part of which engages with the rear surface, that is, the other side of the first block body 42, and to the center of the rear surface of which the cable 15*b* is connected. A wire connection body 44, onto which the wire 41 is hooked is fastened and fixed, with a screw, to the top of the outer circumference of the first block body 42.

The first block body 42 has a circular flange accommodation groove 42*b* so as to communicate with an opening 42*a* formed in the center of the rear surface as shown in FIG. 6 and an inward flange 42*c* is formed around the opening 42*a*. The flange accommodation groove 42*b* also communicates with a cable accommodation section 42*d* which is formed on the front surface of the first block body 42 and has an opening on the front side to which the cable 15*a* is connected and fixed. Furthermore, a circular groove 45*a* with which an O-ring 45 for ensuring watertightness engages is formed in the first block body 42.

The second block body 43 is smaller in outside size than the first block body 42 and has a tapered opening 43*a* formed in the center of the front surface, an outward flange 43*b* formed around the opening 43*a* and a cable accommodation section 43*c* formed so as to communicate with the opening 43*a* and having an opening on the rear side to which the cable 15*b* is connected and fixed.

The outward flange 43*b* of the second block body 43 is accommodated in the flange accommodation groove 42*b* of the first block body 42. The accommodated outward flange 43*b* is held in contact with the inward flange 42*c* of the first block body 42 and the first block body 42 engages with the second block body 43 so as not to separate from each other. Furthermore, the flange accommodation groove 42*b* is designed to be larger in diameter than the outward flange 43*b*. The second block body 43 can freely slide with respect to the first block body 42 in a direction perpendicular to the front-rear direction (axis along the front-rear direction) within a movable range of the outward flange 43*b* in the flange accommodation groove 42*b* (see FIG. 8).

With the first block body 42 engaged with the second block body 43, a plurality of (here two) wires 51 which pass inside skins of the cables 15*a* and 15*b* are wound in coil form and accommodated with certain allowance in the space formed so that the cable accommodation sections 42*d* and 43*c* communicate with each other.

Thus, by being wound in coil form, the wires 51 have a function similar to that of a coil spring that absorbs shake. On the other hand, instead of winding the wires 51, it is also possible to adopt a configuration of simply providing a coil spring for shake absorption in the space formed by the cable accommodation sections 42*d* and 43*c*.

As described so far, the camera system 1 of the present embodiment has a configuration in which the cable shake absorption apparatus 40 which is cable shake preventing means is provided at a halfway point of the cables 15 (15*a*, 15*b*) connected to the camera 2. Thus, when a treatment is applied to the diseased part 100 with the camera 2 being left indwelling and fixed in the abdominal cavity 101 while observing the diseased part 100, even when the trocar 110 through which the cable 15*b* passes and which the cable 15*b* contacts moves or the treatment instrument used contacts the cable 15*b* and interferes (contacts) therewith, the second block body 43 slides with respect to the first block body 42 and absorbs shaking of the cable 15*b*. Therefore, shaking of the cable 15*b* is less likely to be transmitted to the camera 2.

Therefore, as in the case of the first embodiment, during a treatment of the diseased part 100, even when the trocar 110 through which the cable 15*b* passes moves or the treatment instrument or the like interferes (contacts) the cable 15*b* causing the cable 15 to shake, shaking is less likely to occur in an observed image, and the camera 2 can thereby acquire an excellent observed image.

The cable shake absorption apparatus 40 may also be configured to be provided integral with the camera 2.

First Modification Example

As shown in FIG. 9, the camera 2 may also use a rigid body cable 46 for connection with the cable shake absorption apparatus 40. This eliminates the necessity of providing the apparatus lifting wire 41 and the wire connection body 44 for hooking the wire 41 onto the camera 2.

This not only eliminates the operation of the camera system 1 of causing the wire 41 for lifting the cable shake absorption apparatus 40 to penetrate the abdominal wall 102 and pulling the wire 41 from the abdominal cavity 101 to the outside of the body but also eliminates the necessity of puncturing the puncture needle into the abdominal wall, thus providing a minimally invasive configuration that will not impose a burden on the patient compared to the configuration of lifting the cable shake absorption apparatus 40 using the aforementioned wire 41.

Second Modification Example

Furthermore, as shown in FIG. 10 and FIG. 11, the cable shake absorption apparatus 40 may also be configured to have, at the top of the outer circumferential portion thereof, a plurality of (here three) hooking claws 47 to be punctured into and engaged with the abdominal wall 102 and have the wire connection body 44 provided at the top of the front surface of the first block body 42.

The wire connection body 44 is connected to the camera fixing wire 6 for lifting the camera 2 toward the abdominal wall 102 side. Furthermore, as shown in FIG. 12, the camera 2 of the present modification example is configured such that the camera fixing wire 6 is disposed via the suction cup 5 and an insertion section 48 which allows the camera fixing wire 6 to freely advance and retract is formed so that the camera fixing wire 6 extends toward the cable shake absorption apparatus 40 side at the top of the camera 2.

In the camera 2 of the present modification example configured as shown above, the hooking claws 47 of the cable shake absorption apparatus 40 are punctured into the abdominal wall 102 using a treatment instrument such as forceps and the camera fixing wire 6 is lifted to the outside of the body via the abdominal wall 102. The cable shake absorption apparatus 40 then receives tension of the camera fixing wire 6 and is engaged with and fixed to the abdominal wall 102 with the hooking claws 47 being punctured in the abdominal wall 102.

In such a configuration, the camera system 1 also exerts the aforementioned effect according to the present embodiment, need not cause the wire 41 for lifting the cable shake absorption apparatus 40 to penetrate the abdominal wall 102 as in the case of the first modification example, and can thereby provide a minimally intrusive configuration that will not impose a burden on the patient.

The cable shake preventing means according to the present embodiment may be naturally combined with the configuration of the camera 2 according to the first embodiment.

Third Modification Example

Furthermore, as shown in FIG. 13, a wire 49 for lifting the cable shake absorption apparatus 40 may be provided in addition to the camera fixing wire 6 for lifting the camera 2.

Third Embodiment

Next, a third embodiment will be described below based on FIG. 14 to FIG. 16.

Figure 14:
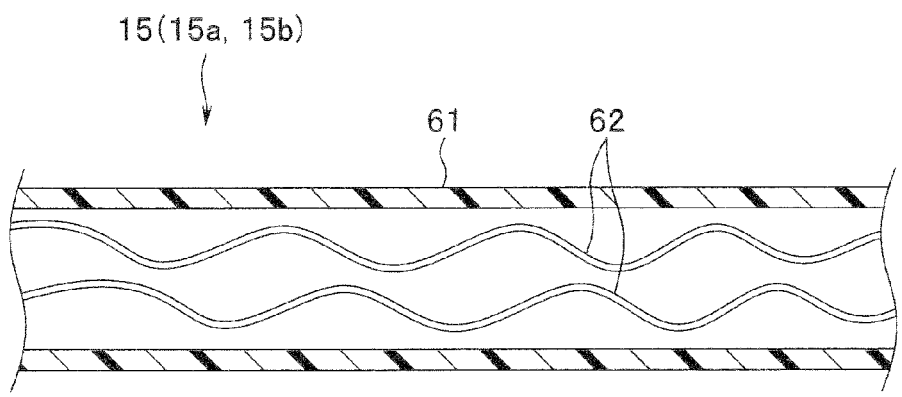
FIG. 14 is related to a third embodiment of the present invention, showing a cross-sectional view illustrating a configuration of a cable that extends from a camera set up in the abdominal cavity.
Figure 15:
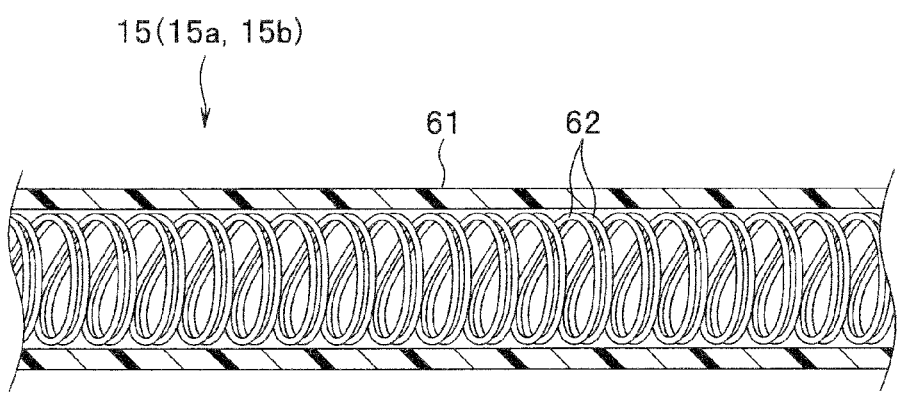
FIG. 15 is a cross-sectional view illustrating a configuration of a cable that extends from a camera set up in the abdominal cavity according to a first modification example of the third embodiment of the present invention.
Figure 16:
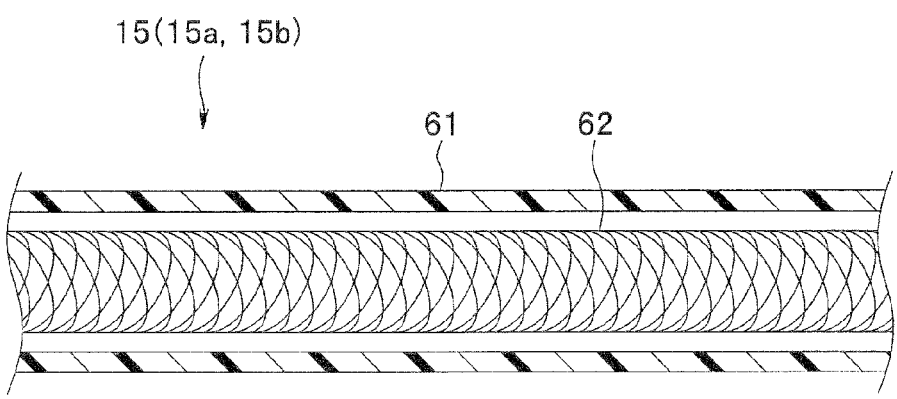
FIG. 16 is a cross-sectional view illustrating a configuration of a cable that extends from a camera set up in the abdominal cavity according to a second modification example of a third embodiment of the present invention.

FIG. 14 to FIG. 16 are related to a third embodiment of the present invention, FIG. 14 is a cross-sectional view illustrating a configuration of a cable, FIG. 15 is a cross-sectional view illustrating a configuration of a cable in a first modification example and FIG. 16 is a cross-sectional view illustrating a configuration of a cable in a second modification example. Furthermore, the following are descriptions of various configurations of the cable 15 (15a, 15b) that extends from the camera 2 set up in the abdominal cavity described in the aforementioned embodiments.

As shown in FIG. 14, the cable 15 (15a, 15b) in the aforementioned embodiments, wires 62 inside a flexible skin 61 are arranged in a randomly or arbitrarily loosened condition with allowance.

Adopting such a configuration, the camera set up in the abdominal cavity 2 left indwelling and fixed in the abdominal cavity 101 can absorb and reduce vibration (shake) using the cable 15 (15a, 15b) itself when applying a treatment to the diseased part 100 while observing the diseased part 100 even when the treatment instrument used contacts the cable 15 (15a, 15b) causing interference contact) therewith and causing an impact on the camera.

First Modification Example

As shown in FIG. 15, even when the wires 62 inside the skin 61 of the cable 15 (15a, 15b) are arranged wound in coil form, such wires themselves can absorb and reduce vibration (shake).

Second Modification Example

Furthermore, as shown in FIG. 16, even when the wires 62 inside the skin 61 of the cable 15 (15a, 15b) are arranged knitted into a braid form, such wires themselves can absorb and reduce vibration (shake).

The invention described so far is not limited to the aforementioned embodiments, but can be implemented modified in various ways without departing from the spirit and scope of the invention in its implementation stages. Furthermore, the respective embodiments include inventions of various stages and various inventions can be extracted by appropriately combining those inventions under a plurality of disclosed configuration requirements.

For example, even when some configuration requirements are removed from all configuration requirements shown in the respective embodiments, if the described effects on the problems to be solved by the invention can be obtained, the configuration from which the configuration requirements are removed can be extracted as an invention.

What is claimed is:

1. A medical apparatus comprising:
    an image pickup apparatus provided for a medical instrument to pick up an image of a region to be examined in a body;
    a fixing section that keeps the image pickup apparatus indwelling in and fixed to a body wall in the body;
    a transmission section that extends from the image pickup apparatus and transmits a power or an electric signal to/from a device outside the body; and
    a shake absorption section arranged in the body as a section independent of the image pickup apparatus, which absorbs and suppresses shaking of the transmission section by means of a movable member connected to the transmission section and accommodated so as to be freely movable in the image pickup apparatus indwelling in and fixed to a body wall, a biasing member for biasing the movable member toward an inside of the image pickup apparatus, and a sealing member for watertightly holding the movable member in a freely movable manner.

2. The medical apparatus according to claim 1, wherein the shake absorption section is arranged at a halfway point of the transmission section.

3. The medical apparatus according to claim 1, further comprising a wire for lifting the shake absorption section toward the body wall side.

4. The medical apparatus according to claim 3, comprising the wire that passes through the fixing section and lifts both the shake absorption section and the image pickup apparatus toward the body wall side.

5. The medical apparatus according to claim 1, wherein the transmission section is a cable in which a wire is arranged in loose form inside a flexible skin.

6. The medical apparatus according to claim 1, wherein the transmission section is a cable in which a wire is arranged wound inside a flexible skin.

7. The medical apparatus according to claim 1, wherein the transmission section is a cable in which a wire is arranged knitted into a braid form inside a flexible skin.

* * * * *

UNITED STATES PATENT AND TRADEMARK OFFICE
CERTIFICATE OF CORRECTION

PATENT NO. : 8,314,836 B2  
APPLICATION NO. : 13/012073  
DATED : November 20, 2012  
INVENTOR(S) : Daisuke Asada et al.

Page 1 of 1

It is certified that error appears in the above-identified patent and that said Letters Patent is hereby corrected as shown below:

Title Page, item (22) should read as follows: Filed: January 24, 2011

Signed and Sealed this  
Second Day of April, 2013

Teresa Stanek Rea  
*Acting Director of the United States Patent and Trademark Office*